US 008765481B2

(12) United States Patent
Waldvogel et al.

(10) Patent No.: US 8,765,481 B2
(45) Date of Patent: Jul. 1, 2014

(54) METHOD FOR DETECTING PEROXIDE EXPLOSIVES

(75) Inventors: Siegfried Waldvogel, Gau-Algesheim (DE); Carsten Siering, Mainz (DE); Daniel Lubczyk, Bornheim (DE)

(73) Assignee: Rheinische Friedrich-Wilhelms-Universitaet Bonn, Bonn (DE)

( * ) Notice: Subject to any disclaimer, the term of this patent is extended or adjusted under 35 U.S.C. 154(b) by 0 days.

(21) Appl. No.: 13/704,243

(22) PCT Filed: Jun. 16, 2011

(86) PCT No.: PCT/EP2011/060052
§ 371 (c)(1),
(2), (4) Date: Dec. 14, 2012

(87) PCT Pub. No.: WO2011/157801
PCT Pub. Date: Dec. 22, 2011

(65) Prior Publication Data
US 2013/0109103 A1    May 2, 2013

(30) Foreign Application Priority Data

Jun. 18, 2010  (WO) ............... PCT/EP2010/058660
Sep. 8, 2010   (DE) ....................... 10 2010 044 756

(51) Int. Cl.
*G01N 33/22* (2006.01)
*G01N 33/00* (2006.01)

(52) U.S. Cl.
USPC .......................................................... 436/92

(58) Field of Classification Search
USPC .......................................................... 436/92
See application file for complete search history.

(56) References Cited

U.S. PATENT DOCUMENTS

| 3,538,011 A | 11/1970 | van der Klaauw |
| 4,455,252 A | 6/1984 | Wylegala et al. |
| 5,648,636 A | 7/1997 | Simpson et al. |
| 2006/0135822 A1 | 6/2006 | Schwarz et al. |
| 2006/0166856 A1 | 7/2006 | Petrat et al. |
| 2006/0183654 A1 | 8/2006 | Small |
| 2007/0001145 A1 | 1/2007 | Faryniarz et al. |
| 2008/0248578 A1 | 10/2008 | Deans et al. |
| 2008/0251169 A1 | 10/2008 | Nicolich et al. |
| 2012/0090744 A1 | 4/2012 | Waldvogel et al. |

FOREIGN PATENT DOCUMENTS

| WO | WO 2004/035018 A2 | 4/2004 |
| WO | WO 2007/005471 A2 | 1/2007 |
| WO | WO 2010/146170 A2 | 12/2010 |

OTHER PUBLICATIONS

S. Pandey: "Analytical applications of room-temperature ionic liquids: A review of recent efforts", Analytica Chimica Acta, vol. 556, pp. 38-45 (2006).

A. Miyake et al.: "Mixing hazard evaluation of organic peroxides with other chemicals", Journal of Loss Prevention in the Process Industries, vol. 18, pp. 380-383 (2005).

R. P. Singh et al.: "Energetic Nitrogen-Rich Salts and Ionic Liquids", Angewandte Chemie, International Edition, vol. 45, No. 22, pp. 3584-3601 (May 26, 2006).

S. Baj et al: "A new method for dialkyl peroxides synthesis in ionic liquids as solvents", Green Chemistry, vol. 8, pp. 292-295 (2006).

P. Wasserscheid et al.: "Ionic Liquids in Synthesis", Wiley-VCH, p. 43 (2003).

S. L. Jain et al.: "[Bmim]BF4-immobilized rhenium-catalyzed highly efficient oxygenation of aldimines to oxaziridines using solid peroxides as oxidants", Jounal of Organometallic Chemistry, vol. 692, pp. 2930-2935 (2007).

P. Rabenecker et al.: "A Look Behind Electrochemical Detection of Explosives", Propellants Explos. Pyrotech., vol. 34, pp. 274-279 (2009).

*Primary Examiner* — Christine T Mui
(74) *Attorney, Agent, or Firm* — Norman B. Thot

(57) ABSTRACT

A method of detecting a peroxidic explosive includes providing a sample which may comprise the peroxidic explosive. A mixture comprising at least one ionic liquid and at least one volatile organic solvent is provided. The sample is taken up in the mixture so as to provide a sample for detection. The sample for detection is analytically detected so as to determine whether it includes the peroxidic explosive.

25 Claims, 1 Drawing Sheet

METHOD FOR DETECTING PEROXIDE EXPLOSIVES

CROSS REFERENCE TO PRIOR APPLICATIONS

This application is a U.S. National Phase application under 35 U.S.C. §371 of International Application No. PCT/EP2011/060052, filed on Jun. 16, 2011 and which claims benefit to International Patent Application No. PCT/EP2010/058660 filed with the PCT on Jun. 18, 2010 and to German Patent Application No. 10 2010 044 756.0, filed on Sep. 8, 2010. The International Application was published in German on Dec. 22, 2011 as WO 2011/157801A1 under PCT Article 21(2).

FIELD

The present invention relates to a method of detecting peroxidic explosives and to a kit comprising the reagents required for the method.

BACKGROUND

Peroxidic explosives such as TATP or HMTD are among the "self elaborates" which can easily be produced in large quantities from household chemicals. The high brisance and thus poor handability of even small amounts of this material is a safety challenge for providing samples of the genuine material. When dissolved in lipophilic ionic liquids, peroxidic explosives such as TATP can be handled safely.

The high brisance of peroxidic explosives makes the analysis of substances discovered extremely dangerous since material must be taken mechanically for doubt-free identification of these pulverulent solids. Dried peroxidic explosives such as TATP and especially HMTD can be detonated in such a procedure. Such discovered substances are usually covered with diesel fuel and, after a certain time, the explosive can be safely collected mechanically. Owing to the complexity of the diesel mixture consisting of several thousand volatile components, later analyses are no longer possible and a forensic valuation is thus impossible.

Stabilization of explosives to achieve a better processability (especially nitro compounds) are described in US 20080251169 A1. Furthermore, S. Baj et al., Green Chemistry 8:292-295 (2006) describe the use of ionic liquids in the synthesis of dialkyl peroxides and WO 2010/146170 describes the use of neutral ionic liquids for stabilizing peroxidic explosives such as TATP or TATP hydrate, for producing stable solutions of peroxidic explosives, and for making these explosives insensitive. Ionic liquids are innovative solvents having a negligible vapor pressure (Ionic Liquids in Synthesis, Eds: P. Wasserscheidt, T. Welton, WILEY-VCH, Weinheim (2003)) which do not influence the olfactory impression of TATP and other peroxidic explosives.

For forensic analysis, samples of high-explosive peroxidic materials such as TATP or HMTD must in particular be safely taken up, stored and analyzed without the sample itself being influenced. For this purpose, diesel oil is presently used, as indicated above, but this not only has a strong odor and, because of the many constituents, interferes in the analysis, but also offers no safety in the handling of peroxidic explosive samples.

SUMMARY

In an embodiment, the present invention provides a method of detecting a peroxidic explosive which includes providing a sample which may comprise the peroxidic explosive. A mixture comprising at least one ionic liquid and at least one volatile organic solvent is provided. The sample is taken up in the mixture so as to provide a sample for detection. The sample for detection is analytically detected so as to determine whether it includes the peroxidic explosive.

BRIEF DESCRIPTION OF THE DRAWINGS

The present invention is described in greater detail below on the basis of embodiments and of the drawings in which.

DETAILED DESCRIPTION

Figure 1:
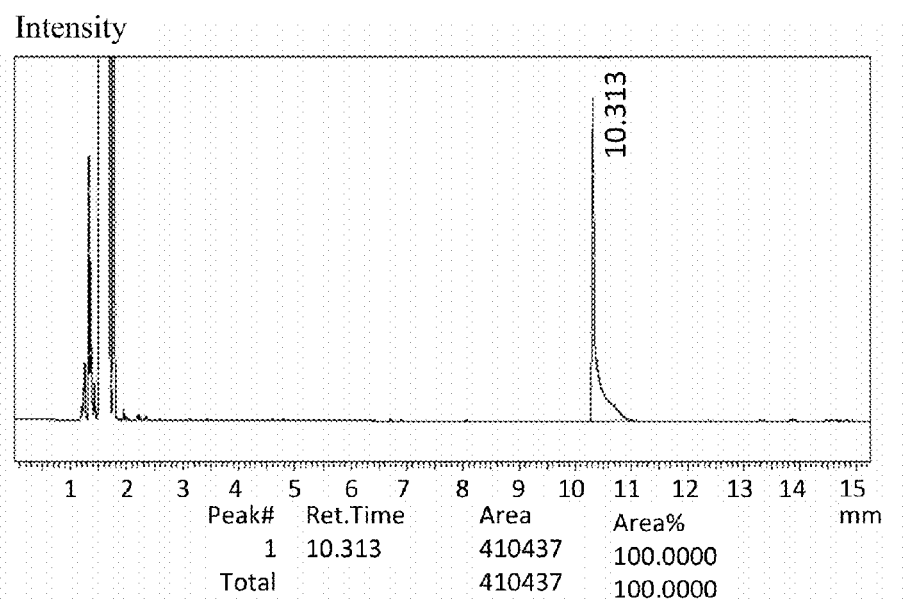
FIG. 1 shows a GC measurement of TATP in a hexane solution. Instrument: GC2010 from Shimadzu, Japan; column: quartz capillary column HP 5 from Agilent, USA (length: 30 m; internal diameter: 0.25 μm); carrier gas: hydrogen; injector temperature: 110° C.; detector temperature: 310° C.; column admission pressure: 68.1 kPa; program: 50° C. start temperature (3 min), 8° C./min heating rate, 100° C. final temperature (6 min)

It has now been found that taking up peroxidic explosives in specific solutions of ionic liquids as are described in WO 04/035018 provides a stable and readily handable form of the explosives with a dramatically reduced mechanical and thermal sensitivity, simple handling in conventional laboratories having standard equipment, and thus allows for an analysis and quantitative determination of the explosive.

The present invention provides a safe method of detecting peroxidic explosives. Selected ionic liquids are used for sampling presumed explosives since these offer excellent protection for the explosive crystals against impact and electrostatic charges. The present invention thus provides:

(1) a method of detecting peroxidic explosives, which comprises taking up of a sample which may contain peroxidic explosives in a mixture of at least one ionic liquid (hereinafter referred to as "IL" for short) and at least one volatile organic solvent and analytical detection of the peroxidic explosive present in the sample; and (2) a kit for a detection method as defined in (1), which comprises a solution consisting of at least one IL and at least one volatile organic solvent.

The present invention provides a forensic working method which is essentially characterized in that suspicious materials are, in the first step, taken up in a mixture of IL and volatile organic solvent ("IL solution") or are wiped off from the sample location using the IL solution. In the second step, the IL sample solution obtained in this way is passed to analysis, e.g., GC/MS, in order to determine the type of explosive and optionally also its content. The method of the present invention is characterized in that the explosive in the IL sample solution obtained is stabilized, this IL solution does not interfere in the analysis and can be safely transported and stored as an exhibit.

In the method according to aspect (1) of the present invention and in the kit according to aspect (2) of the present invention, lipophilic ionic liquids are of particular importance since these absorb less water from the surroundings. Since the properties of ionic liquids are determined both by the cations and by the anions, both sides can be varied. Neutral ionic liquids having a low viscosity can, for example, be used. Suitable lipophilic anions are, inter alia, tetrafluoroborates, triflitimides, perfluoroalkylsulfates, alkylsulfonates, arylsulfonates, perfluoroalkylsulfonates, bis(perfluoroalkyl)sulfonimides, acetates, alkylcarboxylates, isocyanates, isothiocyanates, thiosulfates, halides (including iodides, bromides, chlorides and fluorides), borates, phosphates, nitrates and perchlorates, with tetrafluoroborates and triflitimides being particularly useful. Suitable cations are N-alkyl-substituted nitrogen heterocycles such as N-alkylpyridinium, N-alkylpyrazinium, N-alkylpyridazinium, N-alkylpyrimidinium and bis-N-alkylimidazolium ions, quaternary ammonium and phosphonium ions. Examples include N,N-dialkylimidazolium and N-alkylpyridinium ions. For example, 1-ethyl-3-methylimidazolium bis(trifluoromethane) sulfonimide, 1-butyl-3-methylimidazolium bis(trifluoromethane) sulfonimide, 1-hexyl-3-methylimidazolium bis(trifluoromethane)sulfonimide, 1-ethyl-3-methylimidazolium tetrafluoroborate, 1-hexyl-3-methylimidazolium tetrafluoroborate, 1-octyl-3-methylimidazolium tetrafluoroborate, 1-decyl-3-methylimidazolium tetrafluoroborate, 1-decyl-3-methylimidazolium tetrafluoroborate, N-hexylpyridinium tetrafluoroborate, N-hexylpyridinium bis(trifluoromethane)sulfonimide, N-butyl-3-methylpyridinium tetrafluoroborate, N-butyl-4-methylpyridinium tetrafluoroborate, and mixtures thereof, can be used.

Owing to the nonpolar nature of the TATP molecule, lipophilic ionic liquids are favored. This trend can readily be seen from the solubility of TATP in the 1-alkyl-3-methylimidazolium tetrafluoroborates. At least one alkyl radical of the N,N-dialkylimidazolium ion or the N-alkyl radical of the N-alkylpyridinium being a $C_6$-$C_{16}$-alkyl radical can, for example, be used. It is also possible to use mixtures of the ionic liquids mentioned.

Peroxidic explosives which can be determined according to the present invention are cyclic peroxides such as triacetone triperoxide (TATP), hexamethylene triperoxide diamine (HMTD), diacetone peroxide, etc., having the structures (I) to (III),

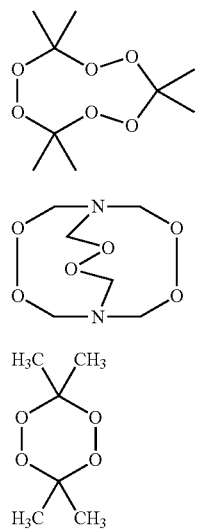

diacyl peroxides of the formula (IV) below, where R is a straight-chain, branched or cyclic, saturated $C_{1-5}$-alkyl radical or a monocyclic or polycyclic aryl radical, where the alkyl and aryl radicals can optionally be substituted by one or more radicals selected from among halogen, nitro, hydroxy and oxo, with diacetyl peroxide and bisbenzoyl peroxide with, for example, the structures (IVa) and (IVb),

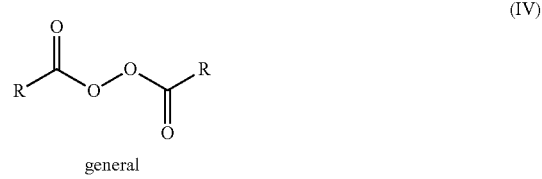

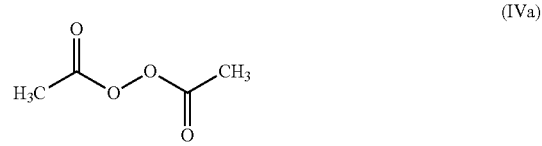

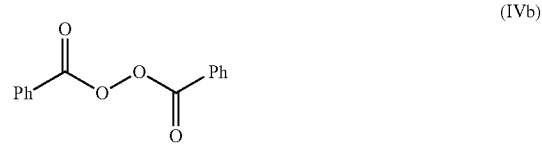

and other easily produced peroxides such as bis(1-hydroxycyclohexyl) peroxide having the formula (V) below

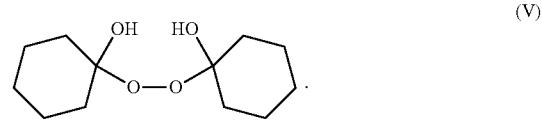 [SMILES: OC1(OOC2(O)CCCCC2)CCCCC1]

In the method according to aspect (1) of the present invention, the IL is used as a mixture with at least one volatile organic solvent. Suitable volatile solvents are solvents which are not readily flammable and which allow for subsequent analysis, including halogenated hydrocarbons such as dichloromethane, chloroform, carbon tetrachloride, 1-chlorobutane and 1,2-dichloroethane, toluene, dimethyl sulfoxide, dimethylformamide, N-methylpyrrolidone, acetonitrile, ethyl acetate, nitromethane, tert-butanol, tert-butyl methyl ether and mixtures thereof. The content of the IL in the volatile solvent is from 1 to 25% by weight, for example, from 5 to 15% by weight.

In an embodiment of the method of aspect (1) of the present invention, the volatile organic solvent is, after the sample has been taken up, evaporated so that the IL together with the peroxidic explosive forms a homogeneous crystalline mass.

The method of the present invention is suitable for both the qualitative analysis and the quantitative analysis of the peroxidic explosive. For quantitative analysis, an adjustment using a calibration sample containing IL and peroxidic explosive can additionally be carried out.

The kit of aspect (2) of the present invention can further contain one or more calibration samples containing an IL and peroxidic explosive. These calibration samples can be a homogeneous crystalline mass as defined above.

The present invention is illustrated by the following examples which do not, however, restrict the scope of protection of the present invention.

EXAMPLES

Example 1

Production of an Ionic Liquid Saturated with Peroxide/TATP

From 20 to 50 ml of the ionic liquid are placed in a 250 ml flask with a magnetic stirrer bar. The flask can, for example, have a wide opening so that pulverulent material can be added easily and the bottom should have a conical shape in order to aid decantation of the liquid after dissolution. The stirrer bar and the magnetic stirrer must have sufficiently strong magnetic fields so that even viscous suspensions can be mixed reliably at a high speed of rotation. The flask is clamped on a magnetic stirrer with stand close to the magnet. The stirrer is set to the highest possible speed of rotation which still allows the stirrer bar to follow the rotation reliably. In practice, the speed of rotation is from 700 to 1000 rpm. 500 mg of the peroxide/triacetone peroxide hydrate (TATP) is added and the flask is closed so as to be gastight. The ground glass stopper is carefully sealed by means of high vacuum grease and clamped shut so that no peroxide can escape during dissolution. The mixture is stirred until the peroxide has completely dissolved. This generally takes from 8 to 12 hours. If the peroxide has not been dissolved completely, mixing is continued for at least another 48 hours to provide a saturated solution. If the peroxide has been dissolved completely, an additional 500 mg of TATP is added and mixing is again continued until either complete dissolution or for 12 hours. This procedure is repeated until undissolved peroxide remains in the solution. The mixture is then stirred for another 48 hours.

When the solutions are saturated, the stirrer is switched off and the solutions are allowed to stand for at least 24 hours. During this time, excess peroxide separates out either on the surface or on the bottom, depending on the density of the liquid. The clear liquid is drawn off very slowly by means of a pipette and dispensed into a securely closed container. The residues of peroxide in the dissolution flask are disposed of using 5% sodium dithionite in an acetone/water mixture (70:30, by weight).

It should be noted that filtration is not possible for the viscous ionic liquids without large losses of material. The excess peroxide therefore must be separated off by decantation or centrifugation. Small amounts of very small crystals remain in the liquid. This very small excess provides that the TATP solutions remain saturated even when small amounts of acetone peroxide escape, e.g., through the seals of the containers. The crystal residues do not represent a hazard due to increased sensitivity because they are present in only small amounts. The properties of the TATP-containing ionic liquids are summarized in Table 1 below.

TABLE 1

Overview of the solubility of TATP in some ionic liquids (ILs)

| Ionic liquid (IL) | M (IL) [g/mol] | rel. TATP integral | C[TATP] (wt.-%) |
|---|---|---|---|
| 1-Ethyl-3-methylimidazolium bis(trifluoromethane)sulfonimide | 391.31 | 0.12 | 0.38 |
| 1-Butyl-3-methylimidazolium bis(trifluoromethane)sulfonamide | 419.36 | 0.32 | 0.94 |
| 1-Hexyl-3-methylimidazolium bis(trifluoromethane)sulfonamide | 447.42 | 0.31 | 0.86 |
| 1-Ethyl-3-methylimidazolium tetrafluoroborate | 197.97 | 0.02 | 0.12 |
| 1-Hexyl-3-methylimidazolium tetrafluoroborate | 254.08 | 0.27 | 1.31 |
| 1-Octyl-3-methylimidazolium tetrafluoroborate | 282.13 | 0.49 | 2.14 |
| 1-Hexyl-3-methylimidazolium iodide | 294.18 | 0.09 | 0.38 |
| 1-Decyl-3-methylimidazolium tetrafluoroborate | 310.18 | 0.32 | 1.27 |
| N-Hexylpyridinium tetrafluoroborate | 251.07 | 0.09 | 0.44 |
| N-Hexylpyridinium bis(trifluoromethane)sulfonimide | 444.41 | 0.33 | 0.92 |
| N-Butyl-3-methylpyridinium tetrafluoroborate | 237.05 | 0.06 | 0.31 |
| N-Butyl-4-methylpyridinium tetrafluoroborate | 237.05 | 0.00 | 0.00 |

Example 2

Determination of the TATP or HMTD Content Via NMR Spectroscopy

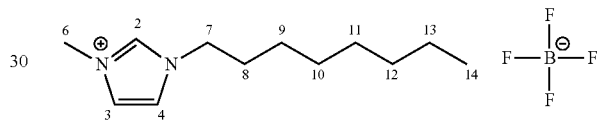

1-Octyl-3-methylimidazolium tetrafluoroborate $^1$H NMR (400 MHz, DMSO-d6): δ=0.85 (t, 3H, H14, $^3$J=8.0 Hz), 1.25 (m, 10H, H9-13), 1.36 (s, 0.49H, CH$_3$ TATP), 1.79 (m, 2H, H8), 3.85 (s, 3H, H6), 4.15 (t, 2H, H7, $^3$J=8.0H), 7.70 (m, 2H, H3-4), 9.04 (s, 1H, H2).

To determine the concentration, the TATP signal at 1.36 ppm is divided by the signal of the methyl group of the imidazole at 3.85 ppm.

$c$(% by weight of TATP)[$M$(TATP)·(TATP signal/6)·100]/$M$($IL$)(1), where $M$(TATP)=222.2 g/mol.

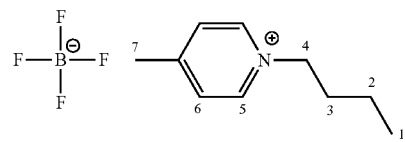

N-Butyl-4-methylpyridinium tetrafluoroborate: $^1$H NMR (400 MHz, DMSO-d6): δ=0.88 (t, 3H, H1, $^3$J$_{1,2}$=8.0 Hz), 1.25 (tq, 2H, H2, $^3$J$_{2,1}$=8.0 Hz, $^3$J$_{2,3}$=8.0 Hz), 1.87 (tt, 2H, H3, $^3$J$_{3,2}$=8.0 Hz, $^3$J$_{3,4}$=6.0 Hz), 2.60 (s, 3H, H7), 4.52 (t, 2H, H4, $^3$J$_{4,3}$=6.0 Hz), 4.65 (d, 0.35H, H$_A$ HMTD, $^3$J$_{HA,HB}$=14.0 Hz), 4.77 (d, 0.35H, H$_B$ HMTD, $^3$J$_{HB,HA}$=14.0 Hz), 7.95 (d, 2H, H6, $^3$J$_{6,5}$=4.0 Hz), 8.86 (d, 2H, H5, $^3$J$_{5,6}$=8.0 Hz).

To determine the concentration of HMTD, the sum of the integrals at 4.65 ppm and 4.77 ppm (corresponds to 12 protons) is divided by the signal of the methyl group of the alkyl chain at 0.88 ppm (corresponds to 3 protons). For simplification, the integrals are adapted during the evaluation so that a value of 3 is obtained for the integral of the IL methyl protons (0.88 ppm).

$$c(HMTD) = \frac{HMTD \text{ signal}/12}{IL \text{ signal}/3} * \frac{M(HMTD)}{M(IL)}$$

Due to the normalization to the methyl protons of the IL, the left-hand lower term becomes 1. For presentation in %, the value is multiplied by 100.

$C(HMTD)=[M(HMDT)\cdot(HMTD \text{ signal}/12)\cdot 100]/M(IL)(1)$, where $M(HMTD)=208.10$ g/mol.

TABLE 2

Overview Solubility of HMTD in Ionic Liquids (ILs)

| Ionic liquid (IL) | M (IL) [g/mol] | rel. HMTD integral[a] | C[HMTD] (wt.-%) |
|---|---|---|---|
| 1-Ethyl-3-methylimidazolium bis(trifluoromethane)sulfonimide | 391.31 | 0.54 | 2.39 |
| 1-Butyl-3-methylpyrolidinium bis(trifluoromethane)sulfonimide | 422.41 | 0.55 | 2.26 |
| N-Hexylpyridinium bis(trifluoromethane)sulfonimide | 444.41 | 0.54 | 2.11 |
| N-Butyl-3-methylpyridinium tetrafluoroborate | 237.05 | 0.23 | 1.68 |
| N-Butyl-3-methylpyridinium tetrafluoroborate | 237.05 | 0.17 | 1.24 |
| N-Butyl-4-methylpyridinium tetrafluoroborate | 237.05 | 0.70 | 5.12 |
| N-Hexylpyridinium tetrafluoroborate | 251.07 | 0.04 | 0.28 |
| 1-Hexyl-3-methylimidazolium bis(trifluoromethane)sulfonimide | 447.42 | 1.17 | 4.53 |
| 1-Ethyl-3-methylimidazolium diethylphosphate | 264.26 | 0.14 | 0.92 |
| 1-Ethyl-3-methylimidazolium methanesulfonate | 206.26 | 0.48 | 4.04 |
| 1-Butyl-1-methylpyrrolidinium trifluoromethanesulfonate | 291.34 | 0.17 | 1.01 |

[a]To calculate the relative signal, the integrals in the NMR are adjusted by normalization of a methyl group of the IL to 3. The relative signal is the sum of the two HMTD proton signals after this normalization and thus represents the integral of the 12 HMTD protons per molecule of IL (see above).

Example 3

Stabilization of Peroxidic Explosives

Stabilization Solution:
10% of 1-hexyl-3-methylimidazolium bis(trifluoromethane)sulfonimide in dichloromethane
Before Stabilizing Treatment:
Sensitivity to friction: HMTD 0.05 N—100% ignition; TATP 0.2 N—100% ignition.
Impact sensitivity: HMTD 0.2 J—100% ignition, TATP 0.5 J—100% ignition.
Stabilization experiments: 100 mg of explosive are moistened with 200 mg of 10% stabilization solution, allowed to dry for 15 minutes and then measured. Within the measurement range, the two stabilized explosives could no longer be ignited: >1 J impact sensitivity and >30 N sensitivity to friction.

Example 4

Safe Sampling of TATP

For sampling, the sample is treated with the desensitizing solution. For this purpose, 5 ml of a solution of 10% 1-methyl-3-octylimidazolium tetrafluoroborate in dichloromethane are added dropwise to or sprayed onto 200 mg of dry TATP. After allowing the solution to act for 5 minutes, a translucent opaque mass is obtained from the colorless crystal powder. This "crystal slurry" can no longer be ignited by impact, static electricity or friction. A sample can be taken safely by means of a spatula. For analytical evaluation/identification, this sample can be evaluated via $^1$H-NMR spectroscopy or gas chromatography. For GC analysis, a small part of the sample (about 20 mg) is covered with a little hexane and the nonpolar phase is injected directly into the GC oven. TATP could clearly be detected/identified via the retention time. The GC spectrum is shown in FIG. 1.

The TAT sample taken is stable for a relatively long time (>2 months). Storage at room temperature or up to 40° C. is possible and does not influence the analytical result. If the samples are stored below room temperature (4-10° C.), large crystals which would be easy to ignite are not formed, but instead a virtually colloidal precipitate which is virtually impossible to separate off by filtration is formed. Over time, the major part of the original sample is converted into this microcrystalline TATP variant.

Figure 2:
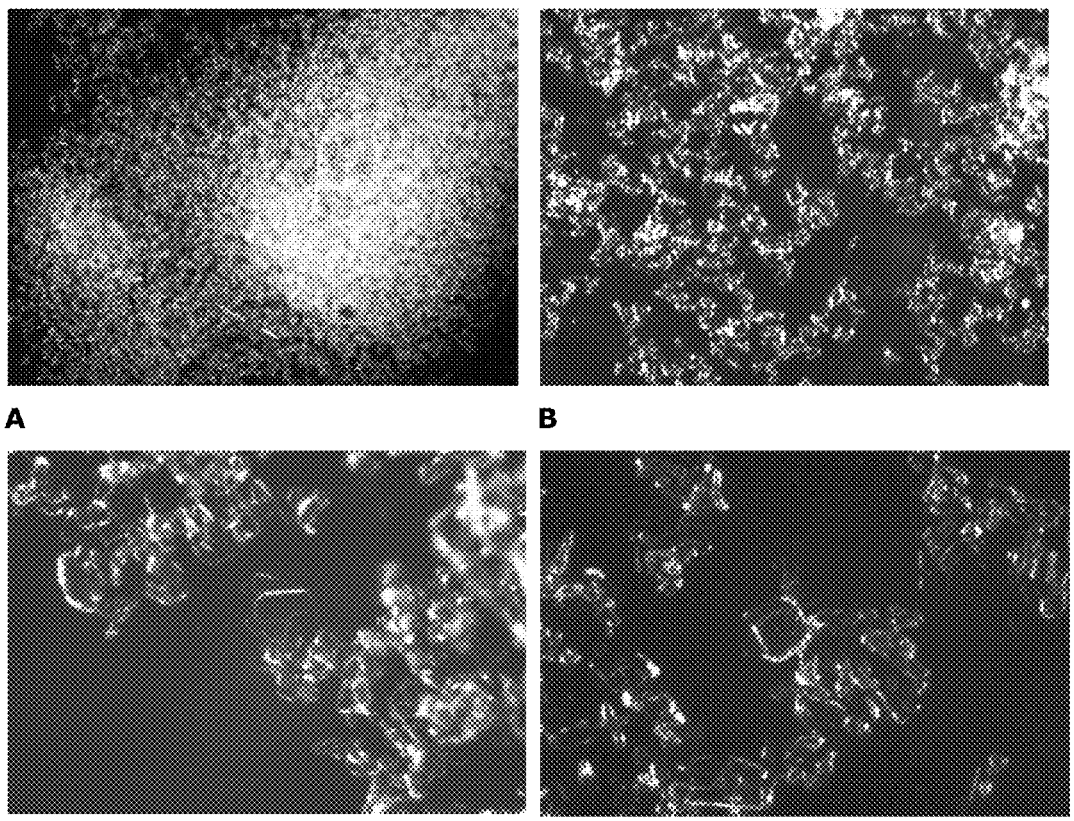
FIG. 2 shows photomicrographs of the crystal slurry of TATP in 1-octyl-3-methylimidazolium tetrafluoroborate; A: 25-fold enlargement, B: 100-fold enlargement, C and D: 260-fold enlargement.

FIG. 2 shows that a mass of similarly sized crystals having a size of 20 μm is formed. The small size and the absence of reaggregation of the crystals is probably due to the action of the ionic liquid as surfactant. Here, the molecules of the ionic liquid become attached by means of their nonpolar side chains to the crystals. This explains the high dispersion in the ionic liquid. A concentration of about 30% of TATP in the crystal slurry examined here was determined by means of NMR spectroscopy. The crystal slurry obtained in this way can still be unambiguously evaluated forensically even after improper handling (exposure, sun, heat, cold).

The present invention is not limited to embodiments described herein; reference should be had to the appended claims.

What is claimed is:

1. A method of detecting a peroxidic explosive, the method comprising:
   providing a sample which may comprise the peroxidic explosive;
   providing a mixture comprising at least one ionic liquid and at least one volatile organic solvent;
   dissolving the sample in the mixture so as to provide a sample for detection; and
   analytically detecting the sample for detection so as to determine whether it includes the peroxidic explosive,
   wherein,
   the sample for detection is stable for >2 months, and
   storage of the sample for detection does not influence an analytical result.

2. The method as recited in claim 1, wherein the analytically detecting is carried out by a spectroscopic method or by a chromatographic method.

3. The method as recited in claim 2, wherein the spectroscopic method is $^1$H-NMR spectroscopy and the chromatographic method is a gas chromatography.

4. The method as recited in claim 1, wherein the at least one ionic liquid is selected from at least one of:
   a tetrafluoroborate,
   a triflitimide,
   a perfluoroalkylsulfate,
   an alkylsulfonate,
   an arylsulfonate,
   a perfluoroalkylsulfonate,
   a bis(perfluoroalkyl)sulfonimide,
   an acetate, an alkylcarboxylate,
an isocyanate,
an isothiocyanate,
a thiosulfate,
a halide,
a borate,
a phosphate,
a nitrate,
a perchlorate salt of N-alkyl-substituted nitrogen heterocycles,
a quaternary ammonium, and
a phosphonium.

5. The method as recited in claim 4, wherein
the perchlorate salt of N-alkyl-substituted nitrogen heterocycles includes N-alkylpyridinium, N-alkylpyrazinium, N-alkylpyridazinium, N-alkylpyrimidinium and bis-N-alkylimidazolium, and
the bis(perfluoroalkyl)sulfonimide includes 1,3-bis-N-alkylimidazolium and N-alkylpyridinium.

6. The method as recited in claim 4, wherein the at least ionic liquid is selected from at least one of:
1-ethyl-3-methylimidazolium bis(trifluoromethane)sulfonimide,
1-butyl-3-methylimidazolium bis(trifluoromethane) sulfon-imide,
1-hexyl-3-methylimidazolium bis(trifluoromethane)sulfonimide,
1-ethyl-3-methylimidazolium tetrafluoroborate,
1-hexyl-3-methylimidazolium tetrafluoroborate,
1-octyl-3-methylimidazolium tetrafluoroborate,
1-decyl-3-methylimidazolium tetrafluoroborate,
1-decyl-3-methylimidazolium tetrafluoroborate,
N-hexylpyridinium tetrafluoroborate,
N-hexylpyridinium bis(trifluoromethane)sulfonimide,
N-butyl-3-methylpyridinium tetrafluoroborate, and
N-butyl-4-methylpyridinium tetrafluoroborate.

7. The method as recited in claim 1, wherein the at least one volatile organic solvent is a solvent which is not readily flammable and allows for the analytically detecting step.

8. The method as recited in claim 7, wherein the at least one volatile organic solvent is selected from at least one of:
a halogenated hydrocarbon,
toluene,
dimethyl sulfoxide,
dimethylformamide,
N-methylpyrrolidone,
acetonitrile,
ethyl acetate,
nitromethane,
tert-butanol, and
tert-butyl methyl ether.

9. The method as recited in claim 8, wherein the halogenated hydrocarbon includes dichloromethane, chloroform, carbon tetrachloride, 1-chlorobutane and 1,2-dichloroethane.

10. The method as recited in claim 1, wherein the mixture is provided as a homogeneous solution.

11. The method as recited in claim 10, wherein a content of the at least one ionic liquid in the mixture is from 1 to 25 wt.-%.

12. The method as recited in claim 11, wherein the content of the at least one ionic liquid in the mixture is from 5 to 15 wt.-%.

13. The method as recited in claim 1, further comprising evaporating the at least one volatile organic solvent in the sample for detection so as to provide a homogeneous crystalline mass comprising the at least one ionic liquid and the peroxidic explosive.

14. The method as recited in claim 1, wherein the peroxidic explosive is selected from:
triacetone triperoxide (TATP),
hexamethylene triperoxide diamine (HMTD),
diacetone peroxide,
a diacyl peroxide of the formula R(C=O)—OO—(C=O)R, wherein R is a straight-chain, a branched or a cyclic, saturated $C_{1-5}$-alkyl radical or a monocyclic or a polycyclic aryl radical, which can optionally be substituted by one or more radicals selected from halogen, nitro, hydroxy, oxo, and
a peroxide which can easily be produced.

15. The method as recited in claim 14, wherein the peroxide which can easily be produced includes bis(1-hydroxycyclohexyl) peroxide.

16. The method as recited in claim 1, wherein, the analytical detection provides a qualitative analysis and a quantitative analysis of the peroxidic explosive.

17. The method as recited in claim 16, wherein for the quantitative analysis, the method further includes:
providing a calibration sample containing the at least one ionic liquid and the peroxidic explosive; and
comparing the sample for detection with the calibration sample.

18. A kit for detecting a peroxidic explosive, the kit comprising:
a solution consisting of:
at least one ionic liquid; and
at least one volatile organic solvent,
wherein the kit is used to detect the peroxidic explosive by a method comprising:
providing a sample which may comprise the peroxidic explosive;
providing the solution;
dissolving the sample in the solution so as to provide a sample for detection; and
analytically detecting the sample for detection to determine whether it includes the peroxidic explosive,
wherein,
the sample for detection is stable for >2 months, and
storage of the sample for detection does not influence an analytical result.

19. The kit as recited in claim 18, wherein:
the at least one ionic liquid is selected from at least one of:
1-ethyl-3-methylimidazolium bis(trifluoromethane) sulfonimide,
1-butyl-3-methylimidazolium bis(trifluoromethane) sulfon-imide,
1-hexyl-3-methylimidazolium bis(trifluoromethane) sulfonimide,
1-ethyl-3-methylimidazolium tetrafluoroborate,
1-hexyl-3-methylimidazolium tetrafluoroborate,
1-octyl-3-methylimidazolium tetrafluoroborate,
1-decyl-3-methylimidazolium tetrafluoroborate,
1-decyl-3-methylimidazolium tetrafluoroborate,
N-hexylpyridinium tetrafluoroborate,
N-hexylpyridinium bis(trifluoromethane)sulfonimide,
N-butyl-3-methylpyridinium tetrafluoroborate, and
N-butyl-4-methylpyridinium tetrafluoroborate, and
the at least one volatile organic solvent is selected from at least one of:
a halogenated hydrocarbon,
toluene,
dimethyl sulfoxide,
dimethylformamide,
N-methylpyrrolidone,
acetonitrile, ethyl acetate,
nitromethane,
tert-butanol, and
tert-butyl methyl ether.

20. The kit as recited in claim 18, further comprising at least one calibration sample comprising the at least one neutral ionic liquid and the peroxidic explosive.

21. The kit as recited in claim 19, wherein the at least one calibration sample is provide as a homogeneous crystalline mass.

22. The method of detecting as recited in claim 1, wherein the at least one ionic liquid is a lipophilic ionic liquid.

23. The method of detecting as recited in claim 1, wherein, prior to analytically detecting the sample for detection so as to determine whether it includes the peroxidic explosive, the method further comprises:
evaporating the volatile organic solvent from the solution.

24. The kit as recited in claim 18, wherein the at least one ionic liquid is a lipophilic ionic liquid.

25. The kit as recited in claim 18, wherein, prior to analytically detecting the sample for detection so as to determine whether it includes the peroxidic explosive, the method further comprises:
evaporating the volatile organic solvent from the solution.

* * * * *